US012712066B2

(12) United States Patent
Miyazaki

(10) Patent No.: US 12,712,066 B2
(45) Date of Patent: Aug. 18, 2026

(54) INFORMATION PROCESSING APPARATUS, CONTROL METHOD FOR INFORMATION PROCESSING APPARATUS, AND STORAGE MEDIUM

(71) Applicant: CANON KABUSHIKI KAISHA, Tokyo (JP)

(72) Inventor: Shigeyuki Miyazaki, Kanagawa (JP)

(73) Assignee: Canon Kabushiki Kaisha, Tokyo (JP)

( * ) Notice: Subject to any disclaimer, the term of this patent is extended or adjusted under 35 U.S.C. 154(b) by 136 days.

(21) Appl. No.: 18/425,929

(22) Filed: Jan. 29, 2024

(65) Prior Publication Data

US 2024/0266031 A1 Aug. 8, 2024

(30) Foreign Application Priority Data

Feb. 3, 2023 (JP) ................................ 2023-015335

(51) Int. Cl.

*G16H 30/40* (2018.01)
*G16H 10/60* (2018.01)

(52) U.S. Cl.

CPC ............. *G16H 30/40* (2018.01); *G16H 10/60* (2018.01)

(58) Field of Classification Search

CPC ........ G16H 30/40; G16H 10/60; G16H 30/20; G16H 50/20

See application file for complete search history.

(56) References Cited

U.S. PATENT DOCUMENTS

| | | | | | |
|---|---|---|---|---|---|
| 5,086,392 | A * | 2/1992 | Nakajima | .............. | H04N 1/217 715/764 |
| 6,108,635 | A * | 8/2000 | Herren | .................. | G16H 10/60 600/300 |
| 10,327,712 | B2 * | 6/2019 | Beymer | ................ | G16H 50/20 |

(Continued)

FOREIGN PATENT DOCUMENTS

| | | | |
|---|---|---|---|
| JP | 2021039683 | A | 3/2021 |

OTHER PUBLICATIONS

Willmen T, Völkel L, Ronicke S, Hirsch MC, Kaufeld J, Rychlik RP, Wagner AD. Health economic benefits through the use of diagnostic support systems and expert knowledge. BMC Health Serv Res. Sep. 9, 2021;21(1):947. doi: 10.1186/s12913-021-06926-y. PMID: 34503507; PMCID: PMC8431907. (Year: 2021).*

(Continued)

*Primary Examiner* — Sun M Li

(74) *Attorney, Agent, or Firm* — Canon U.S.A., Inc. IP Division

(57) ABSTRACT

An information processing apparatus includes a first generation unit configured to generate a list of one or more disease names from an affected area image of a patient, a first determination unit configured to determine a name of a part having an affected area, an acquisition unit configured to acquire a previous medical examination record for the part having the affected area, a second determination unit configured to detect an excluded disease name or an examination result excluding a possibility of a specific disease described in a medical examination history and determine an or the excluded disease name, and a display unit configured to display a disease name or disease names in the list of the one or more disease names that are not described in a list of the excluded disease name, differently from the excluded disease name in the list of the excluded disease name.

13 Claims, 11 Drawing Sheets

(56) References Cited

U.S. PATENT DOCUMENTS

| | | | | |
|---|---|---|---|---|
| 2008/0177578 | A1* | 7/2008 | Zakim | G16H 50/30 705/3 |
| 2010/0082699 | A1* | 4/2010 | Miyasa | G16H 50/20 707/E17.019 |
| 2011/0099032 | A1* | 4/2011 | Miyasa | G16H 50/70 705/2 |
| 2012/0065476 | A1* | 3/2012 | Choi | G16H 40/63 600/300 |
| 2013/0238363 | A1* | 9/2013 | Ohta | G16H 30/20 705/3 |
| 2017/0091413 | A1* | 3/2017 | Kondo | G16H 50/20 |
| 2017/0286604 | A1* | 10/2017 | Kido | G16H 15/00 |
| 2018/0025117 | A1* | 1/2018 | Kanada | G16H 10/60 705/3 |
| 2020/0176123 | A1* | 6/2020 | Kondo | G16H 50/20 |
| 2021/0098089 | A1* | 4/2021 | Choi | G16H 50/20 |
| 2021/0296005 | A1* | 9/2021 | Takahashi | G06F 16/90344 |
| 2021/0375464 | A1* | 12/2021 | Sakaguchi | G16H 10/60 |
| 2022/0175325 | A1* | 6/2022 | Fukushima | G06V 10/82 |
| 2022/0336064 | A1* | 10/2022 | Yoshida | G16H 40/20 |
| 2023/0063218 | A1* | 3/2023 | Yamazaki | G16H 50/30 |

OTHER PUBLICATIONS

C. D. G. Linhares et al., "ClinicalPath: A Visualization Tool to Improve the Evaluation of Electronic Health Records in Clinical Decision-Making," in IEEE Transactions on Visualization and Computer Graphics, vol. 29, No. 10, pp. 4031-4046, Oct. 1, 2023, doi: 10.1109/TVCG.2022.3175626. (Year: 2022).*

L. Dempere-Marco, Xiao-Peng Hu, S. L. S. MacDonald, S. M. Ellis, D. M. Hansell and Guang-Zhong Yang, "The use of visual search for knowledge gathering in image decision support," in IEEE Transactions on Medical Imaging, vol. 21, No. 7, pp. 741-754, Jul. 2002, doi: 10.1109/TMI.2002.801153. (Year: 2002).*

R. Chen, X. Li, S. Huang, L. Shen and M. Wen, "Risk Factors Analysis and Clinical Decision of COPD Based on Machine Learning," 2022 International Conference on Big Data, Information and Computer Network (BDICN), Sanya, China, 2022, pp. 322-330, doi: 10.1109/BDICN55575.2022.00067. (Year: 2022).*

L.-F. Li, X. Wang, W.-J. Hu, N. N. Xiong, Y.-X. Du and B.-S. Li, "Deep Learning in Skin Disease Image Recognition: A Review," in IEEE Access, vol. 8, pp. 208264-208280, 2020, doi: 10.1109/ACCESS.2020.3037258. (Year: 2020).*

* cited by examiner

FIG.5A

FEATURE AMOUNTS FOR INPUT IMAGE

| NAME OF DISEASE | MALIGNANT | FEATURE AMOUNT 1 (DEGREE OF DIFFUSENESS) | FEATURE AMOUNT 2 (DEGREE OF CIRCULARITY) | FEATURE AMOUNT 3 (DEGREE OF REDNESS) | FEATURE AMOUNT 4 (DEGREE OF ROUGHNESS) |
|---|---|---|---|---|---|
| IMAGE | — | 2 | 4 | 3 | 2 |

FIG.5B

FEATURE AMOUNT OF EACH DISEASE

| NAME OF DISEASE | MALIGNANT | FEATURE AMOUNT 1 (DEGREE OF DIFFUSENESS) | FEATURE AMOUNT 2 (DEGREE OF CIRCULARITY) | FEATURE AMOUNT 3 (DEGREE OF REDNESS) | FEATURE AMOUNT 4 (DEGREE OF ROUGHNESS) |
|---|---|---|---|---|---|
| DISEASE A | Y | 5 | 1 | 3 | 4 |
| DISEASE B | N | 2 | 3 | 3 | 2 |
| DISEASE C | Y | 2 | 5 | 3 | 5 |
| DISEASE D | N | 3 | 2 | 4 | 2 |
| DISEASE E | N | 1 | 1 | 5 | 1 |
| DISEASE F | N | 3 | 3 | 1 | 3 |

FIG.5C

DISEASES FOR WHICH SUM OF SQUARES OF DISTANCES OF FEATURE AMOUNTS OF INPUT IMAGE IS LOWER THAN 10

| NAME OF DISEASE | MALIGNANT | SUM OF SQUARES OF DISTANCES | DEGREE OF CERTAINTY |
|---|---|---|---|
| DISEASE B | N | 1 | 80 |
| DISEASE D | N | 6 | 30 |
| DISEASE F | N | 7 | 20 |

FIG.6A

| DISEASE NAME | TIME OF APPEARANCE OF DISEASE | TIME OF COMPLETE CURE OF DISEASE | PART |
|---|---|---|---|
| CONTACT DERMATITIS | APRIL 6, 2020 | AUGUST 6, 2020 | HEAD |
| ATOPIC DERMATITIS | SEPTEMBER 6, 2021 | | HEAD |

FIG.6B

| DISEASE NAME | TIME OF APPEARANCE OF DISEASE | TIME OF COMPLETE CURE OF DISEASE | PART |
|---|---|---|---|
| CONTACT DERMATITIS | APRIL 6, 2020 | AUGUST 6, 2020 | HEAD |
| ATOPIC DERMATITIS | SEPTEMBER 6, 2021 | DECEMBER 6, 2022 | HEAD |

FIG.7A

| No | NAME OF DISEASE | MALIGNANT | DEGREE OF CERTAINTY |
|---|---|---|---|
| 1 | INFECTIOUS DISEASE | N | 80 |
| 2 | COLLAGEN DISEASE | N | 80 |
| 3 | DRUG ERUPTION | N | 80 |
| 4 | HERPES ZOSTER | N | 60 |
| 5 | HIVES | N | 60 |
| 6 | MYCOSIS FUNGOIDES | Y | 10 |

FIG.7B

| No | NAME OF DISEASE | MALIGNANT | DEGREE OF CERTAINTY |
|---|---|---|---|
| 1 | INFECTIOUS DISEASE | N | 80 |
| 2 | COLLAGEN DISEASE | N | 80 |
| 3 | DRUG ERUPTION | N | 80 |
| 4 | ATOPIC DERMATITIS | N | 60 |
| 5 | HIVES | N | 60 |
| 6 | MYCOSIS FUNGOIDES | Y | 10 |

FIG.7C

| No | NAME OF DISEASE | MALIGNANT | DEGREE OF CERTAINTY |
|---|---|---|---|
| 1 | ATOPIC DERMATITIS | N | 80 |
| 2 | MELANOCYTIC NEVUS | N | 80 |
| 3 | MALIGNANT MELANOMA | Y | 10 |

FIG.8A

| DATE OF MEDICAL EXAMINATION | CONTENT OF MEDICAL EXAMINATION BY INTERVIEW | RESULT OF MEDICAL EXAMINATION BY INTERVIEW | EXCLUDED DISEASE NAME | NAME OF PATIENT'S PART |
|---|---|---|---|---|
| AUGUST 6, 2020 | Has drug been administered within past 30 days? | Not administered | DRUG ERUPTION | HEAD |
| MARCH 3, 2021 | Time during which erythema has been seen | Erythema has been seen for three days | | |
| MARCH 3, 2021 | Can erythema disappear in several hours? | No | HIVES | HEAD |
| JANUARY 3, 2022 | Has antimicrobial agent as prescription been applied? | Applied | INFECTIOUS DISEASE | HEAD |

FIG.8B

| EXCLUDED DISEASE NAME |
|---|
| DRUG ERUPTION |
| HIVES |
| INFECTIOUS DISEASE |

FIG.8C

| EXCLUDED DISEASE NAME |
|---|
| HIVES |
| INFECTIOUS DISEASE |

FIG.8D

| EXCLUDED DISEASE NAME |
|---|
| INFECTIOUS DISEASE |

FIG.8E

| EXAMINATION DATE | EXAMINATION ITEM | EXAMINATION RESULT | EXCLUDED DISEASE NAME | NAME OF PATIENT'S PART |
|---|---|---|---|---|
| MARCH 3, 2021 | ANTINUCLEAR ANTIBODY EXAMINATION | NEGATIVE | COLLAGEN DISEASE | |

FIG.8F

| EXCLUDED DISEASE NAME |
|---|
| COLLAGEN DISEASE |
| |

FIG.8G

| EXCLUDED DISEASE NAME |
|---|
| HIVES |
| INFECTIOUS DISEASE |
| COLLAGEN DISEASE |

FIG.9A

| No | NAME OF DISEASE | MALIGNANT | DEGREE OF CERTAINTY |
|---|---|---|---|
| 1 | INFECTIOUS DISEASE | N | 80 |
| 2 | COLLAGEN DISEASE | N | 80 |
| 3 | DRUG ERUPTION | N | 80 |
| 4 | HERPES ZOSTER | N | 60 |
| 5 | HIVES | N | 60 |
| 6 | MYCOSIS FUNGOIDES | Y | 10 |

FIG.9B

| NAME OF DISEASE | MALIGNANT | DEGREE OF CERTAINTY | EXCLUSION |
|---|---|---|---|
| INFECTIOUS DISEASE | N | 30 | EXCLUDED |
| COLLAGEN DISEASE | N | 30 | EXCLUDED |
| DRUG ERUPTION | N | 80 | NOT EXCLUDED |
| HERPES ZOSTER | N | 60 | NOT EXCLUDED |
| HIVES | N | 10 | EXCLUDED |
| MYCOSIS FUNGOIDES | Y | 10 | NOT EXCLUDED |

INFORMATION PROCESSING APPARATUS, CONTROL METHOD FOR INFORMATION PROCESSING APPARATUS, AND STORAGE MEDIUM

BACKGROUND

Field

The present disclosure relates to an apparatus that outputs information on diseases based on images.

Description of the Related Art

In recent years, a diagnosis support system has been devised to reduce the burden on medical doctors in diagnosing patients to identify diseases. Medical doctors often make determinations using temporarily captured images as inputs into such a diagnosis support system. Thus, there is a possibility that some names of possible diseases from the diagnosis support system are ones that medical doctors hardly select as possible diseases. As a result, it can take time and effort for a medical doctor to select an appropriate disease name from enumerated possible disease names.

To address this issue, for example, a technique has been discussed of filtering an output result from a diagnosis support system based on the department or the facility to which a user of the diagnosis support system belongs (Japanese Patent Application Laid-Open No. 2021-039683). This technique enables exclusion of disease names irrelevant to the user from the output of the diagnosis support system.

However, the system described in Japanese Patent Application Laid-Open No. 2021-039683 can only perform filtering based on the affiliation of a user. As a result, there may be no effect of narrowing names of diseases down to the name or names of a disease or diseases that a patient has suffered. In particular, the name of a disease of which the possibility has been excluded with previous medical examinations or examinations can be included. If the name of a disease of which the possibility is excluded often remains among names of possible diseases output by a diagnosis support system, an examination can be performed again, or it can be believed that a result from the diagnosis support system is more reliable than an examination result.

SUMMARY

According to an aspect of the present disclosure, an information processing apparatus that presumes and displays a disease name from an image includes a first generation unit configured to generate a list of one or more disease names from an affected area image of a patient, a first determination unit configured to determine a name of a part having an affected area shown in the affected area image, an acquisition unit configured to acquire a previous medical examination record for the part having the affected area, a second determination unit configured to detect an excluded disease name or an examination result excluding a possibility of a specific disease described in a medical examination history and determine an or the excluded disease name, a listing unit configured to list the excluded disease name, and a display unit configured to display a disease name or disease names in the list of the one or more disease names that are not described in the list of the excluded disease name, differently from the excluded disease name in the list of the excluded disease name.

Further features of the present disclosure will become apparent from the following description of exemplary embodiments with reference to the attached drawings.

BRIEF DESCRIPTION OF THE DRAWINGS

FIGS. 5A to 5C are diagrams illustrating examples of image feature amounts on which the information processing apparatus performs processing according to the exemplary embodiment.

FIGS. 6A and 6B are diagrams illustrating each an example of treatment period information referred to by the information processing apparatus according to the exemplary embodiment.

FIGS. 7A to 7C are diagrams illustrating examples of lists of diseases generated by the information processing apparatus according to the exemplary embodiment.

FIGS. 8A to 8G are diagrams illustrating examples of medical examination and examination result data referred to by the information processing apparatus according to the exemplary embodiment.

FIGS. 9A and 9B are diagrams illustrating examples of lists of diseases before and after correction, generated by the information processing apparatus according to the exemplary embodiment.

DESCRIPTION OF THE EMBODIMENTS

Hereinafter, exemplary embodiments of the present disclosure will be described in detail with reference to the accompanying drawings.

<Information Processing Apparatus>

Figure 1:
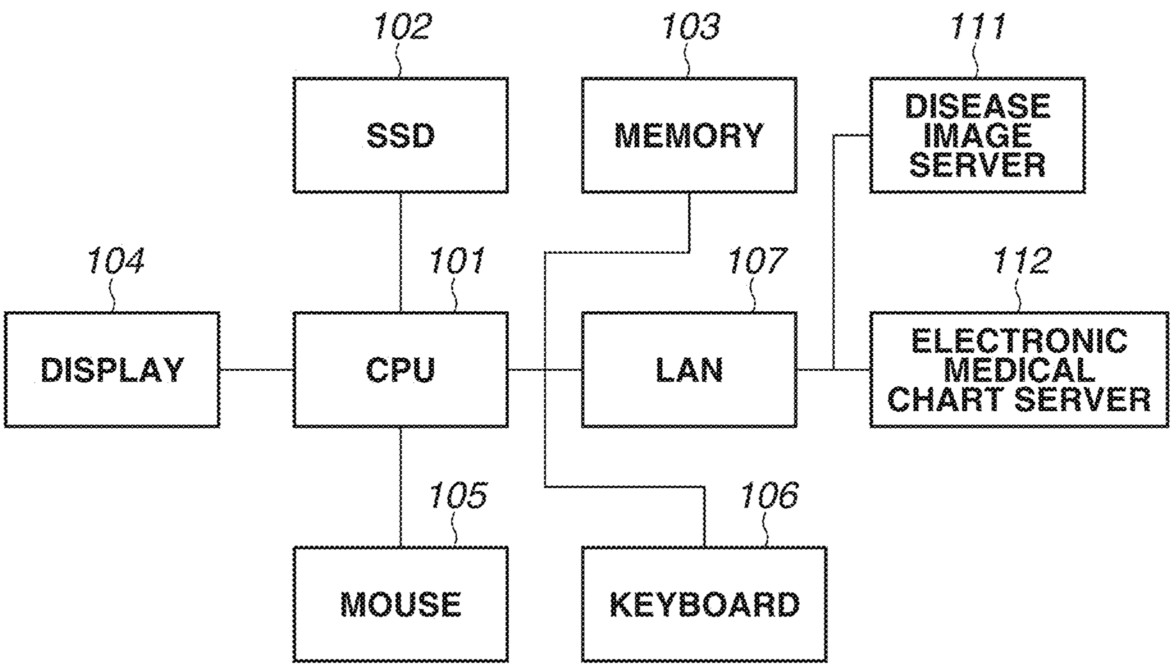
FIG. 1 is a diagram illustrating an example of a schematic configuration of an information processing apparatus according to an exemplary embodiment.

FIG. 1 is a diagram illustrating an example of a schematic configuration of an information processing apparatus according to an exemplary embodiment of the present disclosure.

A central processing unit (CPU) 101 generally controls the information processing apparatus by controlling components of the information processing apparatus. The CPU 101 realizes functions of the information processing apparatus by loading programs recorded in a solid state drive (SSD) 102 into a memory 103 and executing the programs. For the sake of description, the following is a description of a case of one CPU 101 as an example, but the present disclosure is not limited to this. A plurality of CPUs 101 can cooperate with each other to realize functions of the information processing apparatus, or one or more graphics processing units (GPUs) (not illustrated) can cooperate with each other to realize functions of the information processing apparatus.

The memory 103 is a work memory for the operation of CPU 101. The SSD 102 records programs to be executed by the CPU 101. In addition to the programs, images of affected areas showing diseases, previous medical examination histories, and disease image groups and feature amounts thereof are stored for each patient.

A local area network (LAN) 107 communicates with the outside. The LAN 107 is used in acquiring disease images via communication with a disease image server 111 or referring to medical examination histories via communication with an electronic medical chart server 112. The LAN 107 can be wired or wireless. Alternatively, another communication interface can be employed. For example, the information processing apparatus can be designed to communicate with the disease image server 111 and the electronic medical chart server 112 via a mobile phone line or the like.

As input interfaces, a mouse 105 and a keyboard 106 are included in the information processing apparatus. However, the present disclosure is not limited to this configuration. For example, a touch panel employed as a display 104 described below can be an input interface.

The display 104 is used for displaying, for example, results of the CPU 101 executing programs.

<Diagnosis Support Screen>

Figure 2A:
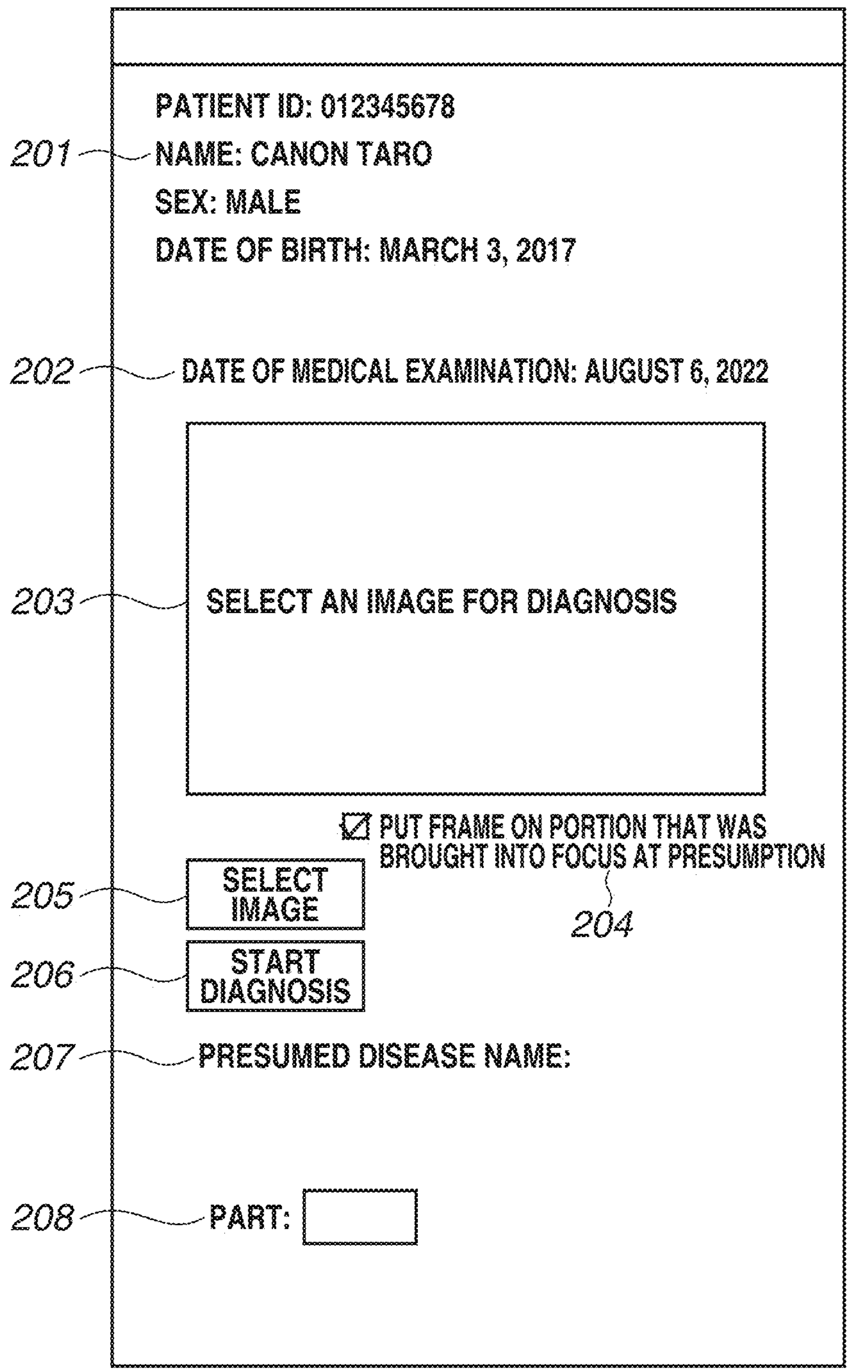
FIGS. 2A to 2C are diagrams illustrating an example of a user interface of the information processing apparatus according to the exemplary embodiment.
Figure 2B:
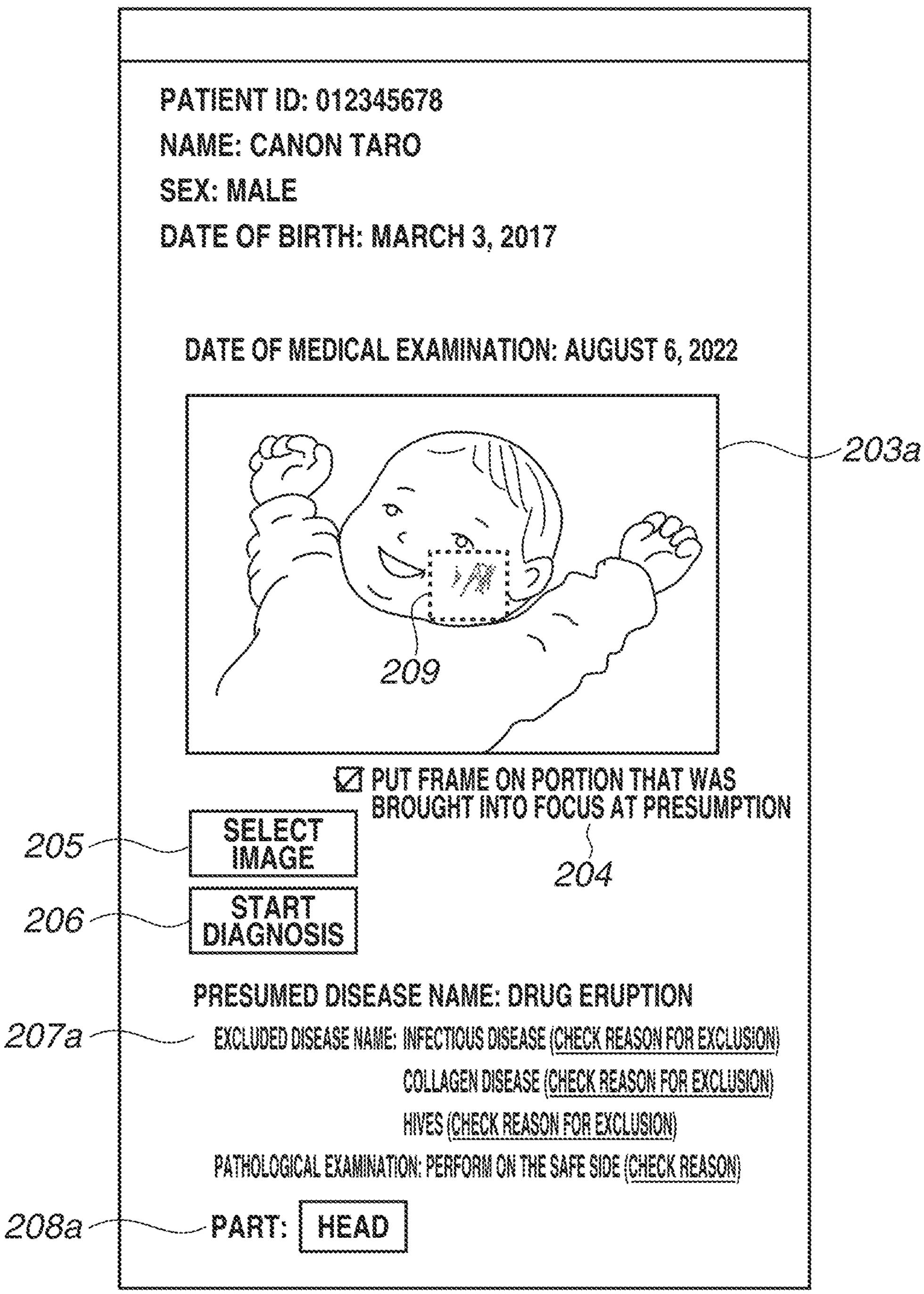
Figure 2C:
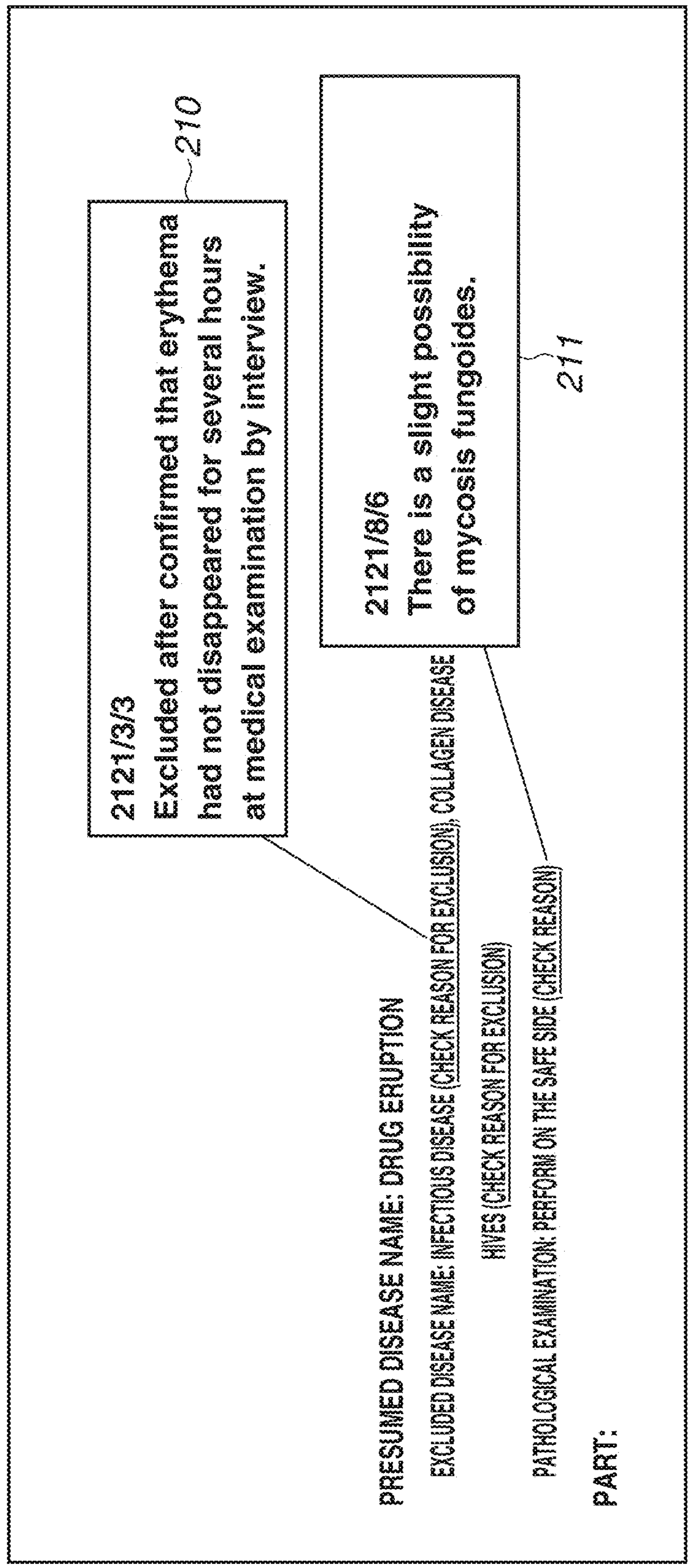

FIGS. 2A to 2C are diagrams illustrating examples of screens for performing diagnosis support. FIG. 2A illustrates a screen before possible diseases are enumerated based on an image, and FIG. 2B illustrates a screen after possible diseases are enumerated. Attribute information 201 displays patient attribute information, such as a patient name. A date of medical examination 202 displays the date on which a medical examination was performed. An image display area 203 displays an image to be diagnosed by the information processing apparatus. A check box 204 switches between display and non-display of a frame for displaying which area of a diagnosed image has been brought into focus. A select-image button 205 is used to select an image to be displayed in the image display area 203. When a user presses the select-image button 205, an image to be displayed in the image display area 203 is selected. Pressing of the select-image button 205 means that the select-image button 205 is selected by a user pressing a predetermined button mounted to the mouse 105 with a mouse cursor being displayed in the display area of the select-image button 205 as an operation of the mouse. As an operation of the touch panel, the pressing of the select-image button 205 means that a touch operation is performed on the display area of the select-image button 205. As an operation of the keyboard 106, the pressing of the select-image button 205 means that the select-image button 205 being brought into focus is selected, for example, with the Enter" key of the keyboard 106. For description purposes, hereinafter, the operations for selection via the above-described various interfaces are collectively referred to as "pressing".

When a start-diagnosis button 206 is pressed, processing for enumerating possible diseases for the image displayed in the image display area 203 is started. A presumed disease name area 207 displays a possible disease or diseases obtained by pressing the start-diagnosis button 206. A part area 208 displays a part of the patient's body (hereinafter referred to just as "part") affected by a disease. The name of a part inferred from the image on the information processing apparatus can either be automatically input or can be input by the user of the information processing apparatus using the keyboard 106.

When an image to be diagnosed is designated using the select-image button 205, the image display area 203 displays the image like an image display area 203*a*. When the user presses the start-diagnosis button 206 while the image is being displayed, the display content of the presumed disease name area 207 changes to that in a presumed disease name area 207*a*, and the part area 208 changes to a part area 208*a*. The presumed disease name area 207*a* displays the name or names of a disease or diseases presumed from the image and the name or names of a disease or diseases presumed from the image but that can be excluded by adding medical examination information up to the current time. The name of a part presumed from the image is displayed in the part area 208*a*. As described above, the name of a part can be rewritten by the user.

<Processing of Diagnosis Support>

Figures 3A, 3B, 3C:
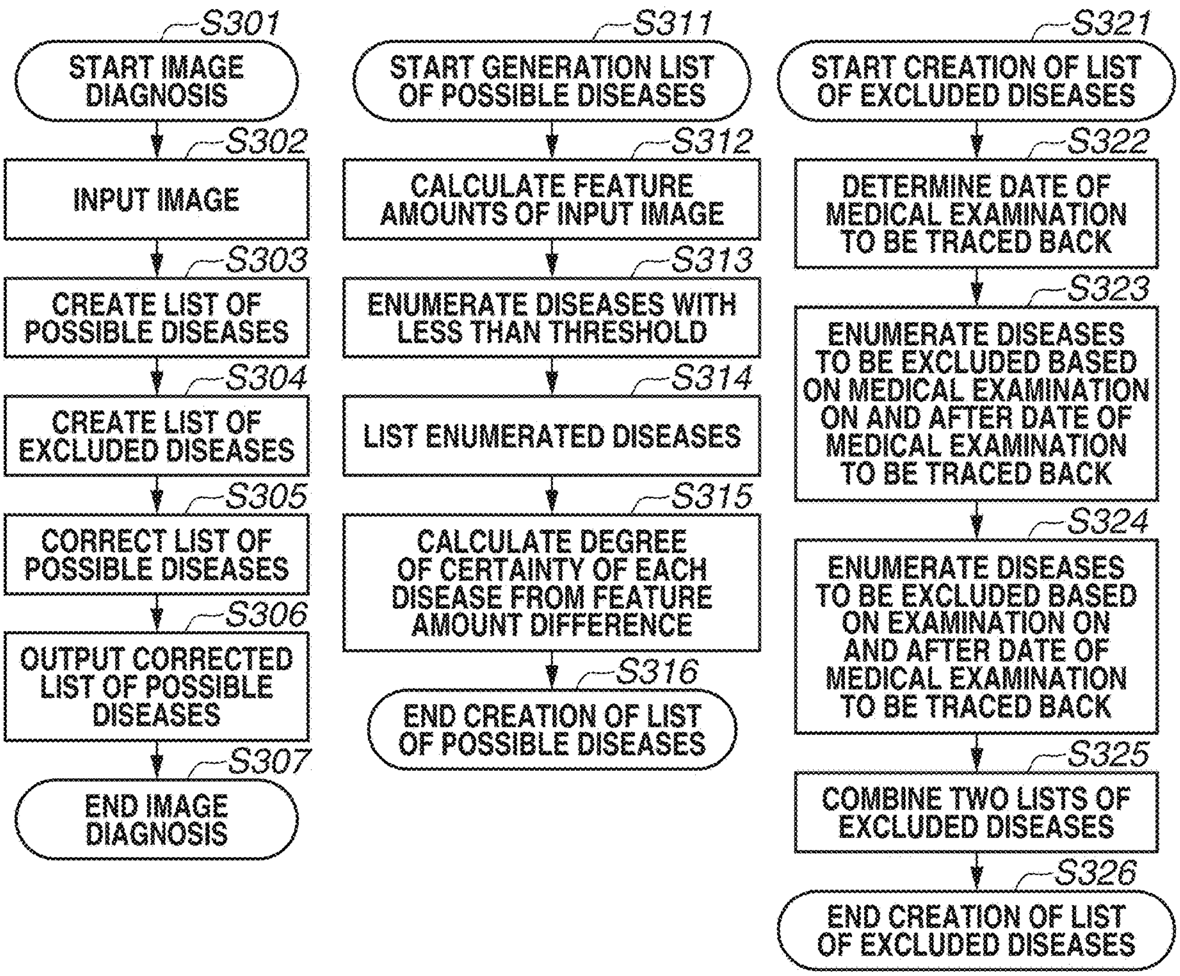
FIGS. 3A to 3C are diagrams illustrating an example of processing of the information processing apparatus according to the exemplary embodiment.

A procedure of processing in the information processing apparatus when the user presses the start-diagnosis button 206 will now be described with reference to the flowchart of FIG. 3A. The processing of the flowchart illustrated in FIG. 3A is carried out by the CPU 101 loading a program into the memory 103 and executing the program. An image diagnosis illustrated by this flowchart starts in step S301 in response to receiving the pressing of the start-diagnosis button 206.

In step S302, the CPU 101 reads the image displayed in the image display area 203*a*.stopped In step S303, the CPU 101 generates a list of possible diseases for the read image. The creation of the list of possible diseases will be described in detail with reference to FIG. 3B, and begins in step S311. In step S312, the CPU 101 calculates feature amounts of the input image. FIG. 5A illustrates an example of the feature amounts to be calculated. In FIG. 5A, four types of feature amount (feature amounts 1 to 4), i.e., the degree of diffuseness, the degree of circularity, the degree of redness, and the degree of roughness, are illustrated for the input image. FIG. 5B illustrates a list of diseases recorded in the information processing apparatus. The four types of feature amount are calculated in advance for each disease. Since any method of calculating feature amounts that feature amounts of an input image and feature amounts of each disease in a list of diseases are calculated can be used, a detailed description of the method of calculating feature amounts from an image is omitted herein.

When the calculation of the feature amounts for the input image is completed, the processing proceeds to step S313, and the CPU 101 enumerates possible diseases that can be inferred from the input image. Specifically, the feature amounts described in the list of diseases in FIG. 5B are compared with the feature amounts for the input image. In the present exemplary embodiment, a disease for which the sum of the squares of the distances of the feature amounts is less than 10 is set as a possible disease obtained from the input image. In the list of diseases in FIG. 5B, diseases with less than 10 are diseases B, D, and F, which can be enumerated as possible diseases.

When the enumeration of possible diseases is completed in step S313, the processing proceeds to step S314. In step S314, the enumerated possible diseases are listed. An example of the listed diseases is illustrated in FIG. 5C. For the information in "name of disease" and "malignant" columns, information in FIG. 5B is used. A "sum of squares of distances" column contains the numerical values calculated in step S313.

In step S314, the list of enumerated diseases is created, and then the processing proceeds to step S315. In step S315, the degrees of certainty for the diseases in the list for the input image are calculated. The degree of certainty is calculated by the following formula: 90−the sum of squares of distances×10. The result is recorded in a "degree of certainty" column in FIG. 5C. Here, the maximum value of the degree of certainty is 90.

When the calculation of the degrees of certainty is completed in step S315, the processing proceeds to step S316. In step S316, the creation of the list of diseases is completed. The above is an example of a method of calculating the degree of certainty.

In the description of the flowchart in FIG. 3B, the possible diseases shown on the input image are enumerated through the comparison of the numerical values of the feature amounts. The comparison method is not limited to thereto. A disease can be inferred by an artificial intelligence (AI) program (a program using AI) capable of calculating the degree of certainty.

The above is a description of the creation of a list of possible diseases. The description now returns to the flowchart in FIG. 3A.

When the creation of the list of possible diseases is completed, the processing proceeds to step S304. In step S304, the creation of a list of excluded diseases is started. The creation of a list of excluded diseases will be described in detail with reference to the flowchart in FIG. 3C, which begins in step S321. First, in step S322, the CPU 101 determines the date of medical examination to be traced back.

Figure 4:
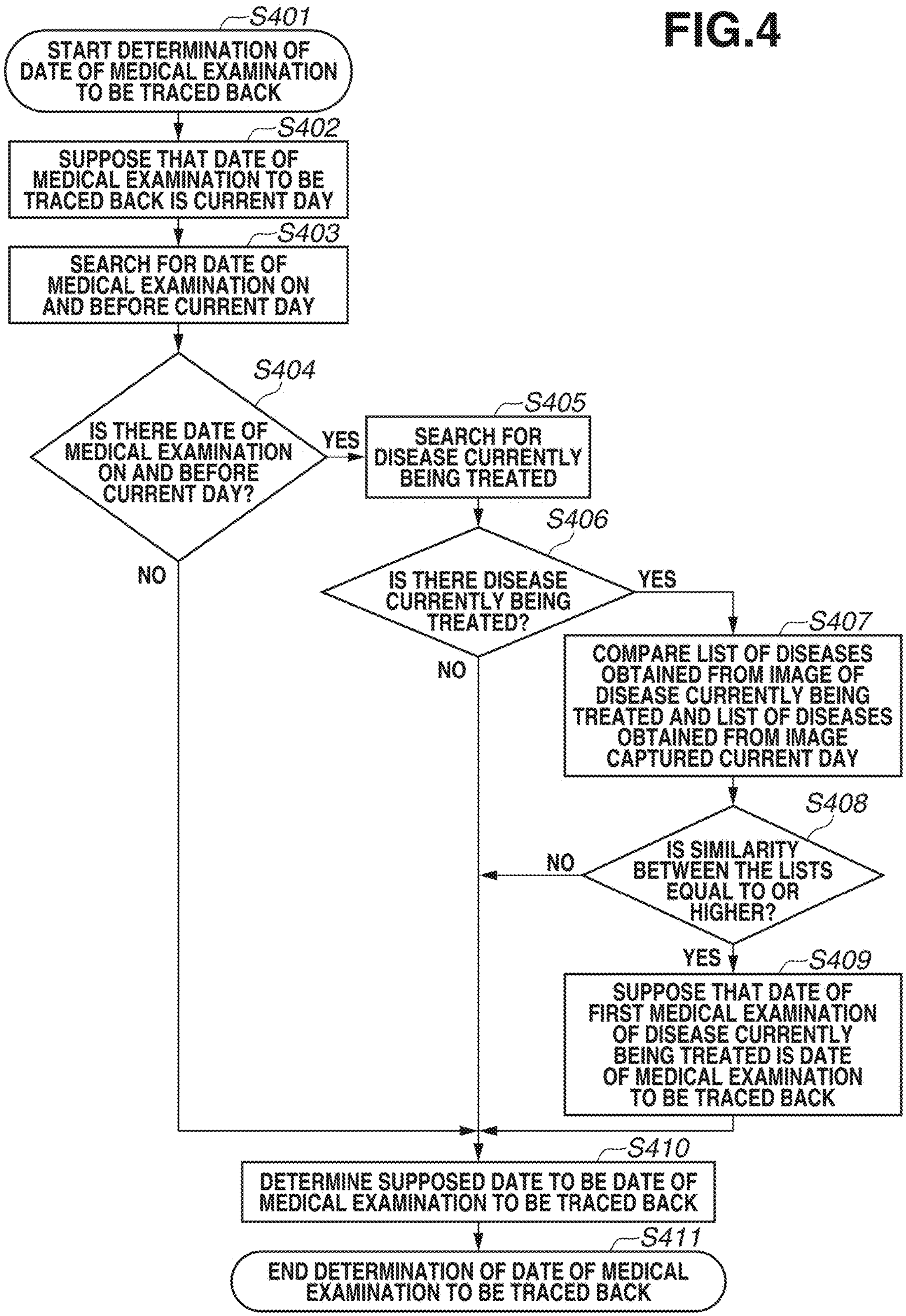
FIG. 4 is a diagram illustrating an example of each piece of processing of the information processing apparatus according to the exemplary embodiment.

In step S322, the CPU 101 determines the date of medical examination to be traced back. Details of the processing of determining the date of medical examination to be traced back will be described with reference to the flowchart in FIG. 4, which begins in step S401.

In step S402, the CPU 101 supposes that the date of medical examination to be traced back is the current day when the user is operating the information processing apparatus. Then, in step S403, the CPU 101 searches for a history of performing medical examination on the same patient on a date before the current day. Specifically, the CPU 101 refers to information on a medical examination history of an electronic medical chart.

In step S404, the CPU 101 determines whether information on a date of medical examination before the current day is in the medical examination history. If no information on a date of medical examination before the current day is in the medical examination history (NO in step S404), the processing proceeds to step S410. In step S410, the CPU 101 determines the supposed date of medical examination to be the date of medical examination to be traced back. Then, in step S411, the procedure for determining the date of medical examination to be traced back ends.

If the record of a medical examination that has been made before the current day is found in step S404 (YES in step S404), the processing proceeds to step S405. In step S405, the CPU 101 searches the medical examination record for a disease currently being treated. In step S406, the CPU 101 determines if there is a disease that is currently being treated. If in step S406, the CPU 101 determines there is a disease currently being treated, the flow proceeds to step S407. If the CPU 101 determines there is no disease currently being treated, the flow proceeds to step S410.

FIGS. 6A and 6B illustrate examples of medical examination records. When, for example, the date of Mar. 3, 2022, is the date of the current day when the information processing apparatus is being operated, the medical examination records illustrated in FIG. 6A indicate that medical examinations have been performed before Mar. 3, 2022. More specifically, the medical examination records indicate that the part of the body examined was the head, and the diseases have occurred in the same part as the part input to the part area 208 described above. As illustrated in FIG. 6A, medical examination record indicates that the atopic dermatitis is not completely cured. As illustrated in FIG. 6B, the medical examination record indicates that the atopic dermatitis is completely cured.

Information on complete cure in a medical examination record can be manually input as, for example, "complete cure" by a medical doctor. The information can also be automatically input as, for example, "complete cure" when a list of diseases is output from a captured image and no disease that should be currently being treated is described.

Turning back to FIG. 4, in the case of, for example, the medical examination record of FIG. 6A, i.e., disease currently being treated, in step S407, in order to determine if a disease or diseases subject to a medical examination on the current day is or are the same as a disease or diseases that has or have been being treated, the CPU 101 compares the diseases in lists of diseases from images at the medical examinations. Examples of the lists of diseases at the medical examinations are illustrated in FIGS. 7A to 7C. FIG. 7A is the list of diseases obtained from the image at the medical examination on the current day. FIG. 7B is the list of diseases obtained from an image of a lesion that has been being treated.

To measure the similarities between the lists, first, a value is obtained by the expression "the number of types of disease described in both the lists "÷" the number of types of diseases described in at least one of the lists". This value is referred to as a value $\alpha$. In the present exemplary embodiment, if the value $\alpha$ is greater than or equal to 0.6, the lists are similar, and it is determined that the medical examination on the current day is a continuation of the treatment of a disease or diseases in the previous medical examination.

Comparing FIG. 7A and FIG. 7B, the number of types of diseases listed in both the lists is 5, and the number of types of diseases listed in at least one of the lists is 7. As the result, the value $\alpha$ is 0.625, and it is determined that the two lists are similar to each other, and that the treatment of the disease or the diseases that has or have been being treated is continued.

If the list of diseases obtained from the image of the lesion that has been being treated is a list of diseases in FIG. 7C, the number of types of diseases described in both the lists of FIGS. 7A and 7C is 0, and the number of types of diseases described in at least one of the lists is 9. As the result, the value $\alpha$ is 0, and it is determined that the two lists are not similar. Consequently, it is determined that a disease or diseases that has or have been being treated is or are not subject to the current medical examination or has or have been completely cured before the current medical examination.

The lists of diseases are compared in step S407, and in step S408, if each similarity between the lists is lower than a threshold, the processing proceeds to step S410. If each similarity is equal to or higher than the threshold, the processing proceeds to step S409. In step S409, the CPU 101 supposes that the date of the first medical examination of a disease or diseases currently being treated is the date of medical examination to be traced back. The processing then proceeds to step S410.

When the date of medical examination to be traced back is determined in step S322, the processing proceeds to step S323. In step S323, the CPU 101 enumerates diseases to be excluded based on a medical examination or medical examinations on and after the date of medical examination to be traced back. FIGS. 8A to 8G illustrate examples of data on medical examination by interview and examination result data recorded in the electronic medical chart. A disease or diseases that has or have been excluded can be obtained via medical examination by interviewing the patient by a medical doctor or medical doctors. The disease to be added to a list of excluded diseases depends on the date of medical examination to be traced back determined in step S322.

When the date of medical examination to be traced back is Aug. 6, 2020, a list of excluded diseases determined based on the medical examination(s) is illustrated in FIG. 8B. When the date of medical examination to be traced back is Mar. 3, 2021, a list of excluded diseases is illustrated in FIG. 8C. When the date of medical examination to be traced back is Jan. 3, 2022, a list of excluded diseases is illustrated in FIG. 8D.

Returning to FIG. 3C, the processing then proceeds to step S324. In step S324, the CPU 101 enumerates diseases to be excluded based on an examination or examinations.

An example of examination result data is illustrated in FIG. 8E. The result of an antinuclear antibody examination on Mar. 3, 2021, was negative, indicating that collagen disease is an excluded disease. That is, the CPU 101 detects collagen disease as an excluded disease based on the examination result. When the date of medical examination to be traced back is Mar. 3, 2021, or earlier, a list of excluded diseases determined based on an examination or examinations is illustrated in FIG. 8F. When the date of medical examination to be traced back is Mar. 4, 2021, or later, there is no list of excluded diseases determined based on the examination(s).

Returning to FIG. 3C, after the diseases to be excluded based on the examination(s) are distinguished, the processing proceeds to step S325. In step S325, the CPU 101 combines the list of excluded diseases based on the medical examination(s) and the list of excluded diseases based on the examination(s). The diseases described in the two lists are simply added. For example, when the date of medical examination to be traced back is Mar. 3, 2021, the list of excluded disease names of FIG. 8C and the list of excluded disease name in FIG. 8F are added to generate a list of excluded disease names in FIG. 8G. After the processing in step S325, the processing proceeds to step S326. In step S326, the creation of a list of excluded diseases ends.

Returning to FIG. 3A, after the list of excluded diseases is created in step S304 as described above, in step S305, the CPU 101 corrects the list of possible diseases.

As an example correcting the list of possible diseases, FIGS. 9A and 9B illustrate lists before and after the correction. FIG. 9A is the list of possible diseases created in step S303 for the image at the time of the medical examination. FIG. 9B illustrates a list of possible diseases after the correction. In the list of FIG. 9B, the number of disease names is the same as those in the list of FIG. 9A, but the degrees of certainty of the three diseases (collagen disease, hives, and infectious disease) described in FIG. 8G are each reduced by 50 with respect to the list of FIG. 9A. A value of 50 as the amount of reducing the degree of certainty is merely an example. The amount of subtraction can be changed depending on the reason for exclusion.

Returning to FIG. 3A, after the CPU 101 corrects the list of possible diseases in step S305, in step S306, the CPU 101 outputs the corrected list of possible diseases. Specifically, the corrected list of possible diseases is displayed in the presumed disease name area 207*a*. In the presumed disease name area 207*a* according to the present exemplary embodiment, the contents of the corrected list of possible diseases are displayed per the following rules. First, only presumed disease names with the degree of certainty exceeding 70 are displayed. However, even if the degree of certainty is less than 70, an excluded disease name is displayed so that it can be understood that the disease name is excluded for some reason. The reason for the exclusion can be checked with a tooltip as in a reason 210 illustrated in FIG. 2C by, for example, performing a mouse-over operation on the name of the excluded disease with the mouse 105.

Even if the degree of certainty is low, a character string recommending a pathological examination for a disease classified as malignant is displayed in the presumed disease name area 207*a*. The reason for recommending a pathological examination can be checked with a tooltip as in the reason 211 illustrated in FIG. 2C by, for example, by performing a mouse-over operation with the mouse 105.

In the above description, a disease is excluded based on medical examination by interview or examination, but another method can be used. In another exemplary embodiment, for diseases, such as tinea unguium and hand eczema, where the part where the disease occurs is typically limited, if the part designated in the part area 208*a* and the part where the disease occurs are not the same, the disease can be added to the list of excluded diseases for that reason.

The amount of change in the size of a lesion area obtained by image-capturing a part at different dates and times can be calculated and used to determine whether the type of disease is chronic or acute. If the amount of change is greater than or equal to a threshold in a predetermined period, a chronic disease can be added to a list of excluded diseases. If the amount of change is less than the threshold in the predetermined period, an acute disease can be added to the list of excluded diseases.

As described above, the limitation of the display of an inappropriate disease name or a disease name that has been determined not to be a corresponding disease enables medical doctors to save time and effort to select the correct corresponding disease name.

While the exemplary embodiment of the present disclosure has been described above, the present disclosure is not limited thereto, and various modifications and changes can be made within the scope of the gist of the present invention.

The present disclosure can also be realized by processing in which a program for realizing one or more functions of the above-described exemplary embodiment is supplied to a system or an apparatus via a network or a storage medium, and one or more processors in a computer of the system or the apparatus read and execute the program. The present disclosure can also be realized by a circuit (for example, an application-specific integrated circuit [ASIC]) that realizes one or more functions.

Other Embodiments

Embodiment(s) of the present disclosure can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc™ (BD)), a flash memory device, a memory card, and the like.

While the present disclosure has been described with reference to exemplary embodiments, it is to be understood that the disclosure is not limited to the disclosed exemplary embodiments. The scope of the following claims is to be accorded the broadest interpretation so as to encompass all such modifications and equivalent structures and functions.

This application claims the benefit of Japanese Patent Application No. 2023-015335, filed Feb. 3, 2023, which is hereby incorporated by reference herein in its entirety.

What is claimed is:

1. An information processing apparatus that provides diagnosis support by presuming and displaying at least one disease name from an image, the information processing apparatus comprising:

at least one memory storing a program and storing disease data in which each of a plurality of disease names is associated with feature amounts; and at least one processor that executes the program to cause the information processing apparatus to:

read an image of a part of a patient affected by a disease;

calculate feature amounts of the image, the feature amounts including a degree of diffuseness, a degree of circularity, a degree of redness, and a degree of roughness;

generate a list of one or more disease names from the feature amounts, by:

(i) comparing the feature amounts of the image with the feature amounts associated with each disease name stored in the disease data, (ii) calculating, for each disease name, a sum of squares of distances of the feature amounts, and (iii) enumerating one or more disease names for which the sum of squares of distances is lower than a threshold;

calculate, for each enumerated disease name, a degree of certainty based on the calculated sum of squares of distances;

determine a name of the part of the patient in the image that is affected by the disease;

acquire a previous medical examination record for the part affected by the disease;

detect an excluded disease name or an examination result excluding a possibility of a specific disease described in a medical examination history;

determine the excluded disease from the detected excluded disease name or an excluded disease name from the examination result;

generate a list of at least one excluded disease name;

correct the list of the one or more disease names by reducing, by a predetermined numerical value, a degree of certainty of a disease name included in the list of at least one excluded disease name; and display at least one disease name in the list of the one or more disease names that are not included in the list of the excluded disease name differently from the excluded disease name in the list of the excluded disease name, wherein:

an excluded disease name is displayed in a form indicating exclusion, a reason for exclusion is displayed in response to a mouse-over operation on the displayed excluded disease name, and a character string recommending a pathological examination is displayed for a disease classified as malignant, and a reason for recommending the pathological examination is displayed in response to a mouse-over operation;

wherein the processor further causes the information processing apparatus to:

determine whether a disease has been previously completely cured when the excluded disease name is determined; and determine an excluded disease name only from a medical examination history of a disease determined to not be completely cured, wherein the processor further causes the information processing apparatus to compare a list of one or more disease names generated from a current medical examination image with a list of one or more disease names generated from a previous medical examination image, and wherein, when an amount of change is greater than or equal to a threshold, a previous medical examination history before the current medical examination is not referred to even when the disease of the previous medical examination is not completely cured and the excluded disease name is determined regardless of the previous medical examination history.

2. The information processing apparatus according to claim 1, wherein the processor further causes the information processing apparatus to determine that a specific disease is completely cured when an indication that the specific disease has been completely cured is included in the medical examination history.

3. The information processing apparatus according to claim 2 wherein the specific disease is a lesion and the processor further causes the information processing apparatus to determine that the lesion is completely cured when an area indicating a lesion in a captured image at a previous medical examination is not present in a subsequently captured image.

4. The information processing apparatus according to claim 1, wherein the determined excluded disease name is a disease name indicated as an exclusion in the medical examination history.

5. The information processing apparatus according to claim 1, wherein the determined excluded disease name is a disease name of which a possibility is excluded with the examination result recorded in the medical examination history.

6. The information processing apparatus according to claim 1, wherein the determined excluded disease name is a disease name unrelated to the part of the patient.

7. The information processing apparatus according to claim 6, wherein information on the part of the patient affected by a disease can be input by a user or input based on the image of the part of the patient affected by a disease.

8. The information processing apparatus according to claim 1, wherein the processor further causes the information processing apparatus to display the determined excluded disease name in a form indicating the exclusion.

9. The information processing apparatus according to claim 8, wherein the processor further causes the information processing apparatus to display a reason for the exclusion of the displayed excluded disease name.

10. The information processing apparatus according to claim 1, wherein the processor further causes the information processing apparatus to calculate a name of a possible disease and a degree of certainty of the possible disease, and to determine that the name of the possible disease is to be excluded, wherein the degree of certainty of the name of the possible disease is reduced by a predetermined numerical value.

11. The information processing apparatus according to claim 1, wherein the processor further causes the information processing apparatus to calculate a size of a lesion from an image of the part of the patient previously captured, wherein a chronic disease is to be excluded when a calculated amount of change in the size of the lesion is greater than or equal to a predetermined amount, and wherein an acute disease is to be excluded when the calculated amount of change in the size of the lesion is less than the predetermined amount.

12. A method for controlling an information processing apparatus that provides diagnosis support by presuming and displaying at least one disease name from an image, the method comprising:

reading an image of a part of a patient affected by a disease;

calculating feature amounts of the image, the feature amounts including a degree of diffuseness, a degree of circularity, a degree of redness, and a degree of roughness;

generating a list of one or more disease names from the feature amounts, by:

(i) comparing the feature amounts of the image with feature amounts associated with each of a plurality of disease names stored in disease data;

(ii) calculating, for each disease name, a sum of squares of distances of the feature amounts, and (iii) enumerating one or more disease names for which the sum of squares of distances is lower than a threshold;

calculating, for each enumerated disease name, a degree of certainty based on the calculated sum of squares of distances;

determining a name of the part of the patient in the image that is affected by the disease;

acquiring a previous medical examination record for the part affected by the disease;

detecting an excluded disease name or an examination result excluding a possibility of a specific disease described in a medical examination history;

determining the excluded disease from the detected excluded disease name or an excluded disease name from the examination result;

generating a list of at least one excluded disease name;

correcting the list of the one or more disease names by reducing, by a predetermined numerical value, a degree of certainty of a disease name included in the list of at least one excluded disease name; and displaying at least one disease name in the list of the one or more disease names that are not included in the list of the excluded disease name differently from the excluded disease name in the list of the excluded disease name, wherein:

an excluded disease name is displayed in a form indicating exclusion, a reason for exclusion is displayed in response to a mouse-over operation on the displayed excluded disease name, and a character string recommending a pathological examination is displayed for a disease classified as malignant, and a reason for recommending the pathological examination is displayed in response to a mouse-over operation;

determining whether a disease has been previously completely cured when the excluded disease name is determined;

determining an excluded disease name only from a medical examination history of a disease determined to not be completely cured; and comparing a list of one or more disease names generated from a current medical examination image with a list of one or more disease names generated from a previous medical examination image, wherein, when an amount of change is greater than or equal to a threshold, a previous medical examination history before the current medical examination is not referred to even when the disease of the previous medical examination is not completely cured and the excluded disease name is determined regardless of the previous medical examination history.

13. A non-transitory computer-readable storage medium storing a computer-readable program for causing a computer to execute a method to control an information processing apparatus that provides diagnosis support by presuming and displaying at least one disease name from an image, the method comprising:

reading an image of a part of a patient affected by a disease;

calculating feature amounts of the image, the feature amounts including a degree of diffuseness, a degree of circularity, a degree of redness, and a degree of roughness;

generating a list of one or more disease names from the feature amounts of the image of a part of a patient affected by the disease, by:

(i) comparing the feature amounts of the image with feature amounts associated with each of a plurality of disease names stored in disease data;

(ii) calculating, for each disease name, a sum of squares of distances of the feature amounts, and (iii) enumerating one or more disease names for which the sum of squares of distances is lower than a threshold;

calculating, for each enumerated disease name, a degree of certainty based on the calculated sum of squares of distances;

determining a name of the part of the patient in the image that is affected by the disease;

acquiring a previous medical examination record for the part affected by the disease;

detecting an excluded disease name or an examination result excluding a possibility of a specific disease described in a medical examination history;

determining the excluded disease from the detected excluded disease name or an excluded disease name from the examination result;

generating a list of at least one excluded disease name;

correcting the list of the one or more disease names by reducing, by a predetermined numerical value, a degree of certainty of a disease name included in the list of at least one excluded disease name; and displaying at least one disease name in the list of the one or more disease names that are not included in the list of the excluded disease name differently from the excluded disease name in the list of the excluded disease name, wherein:

an excluded disease name is displayed in a form indicating exclusion, a reason for exclusion is displayed in response to a mouse-over operation on the displayed excluded disease name, and a character string recommending a pathological examination is displayed for a disease classified as malignant, and a reason for recommending the pathological examination is displayed in response to a mouse-over operation;

determining whether a disease has been previously completely cured when the excluded disease name is determined;

determining an excluded disease name only from a medical examination history of a disease determined to not be completely cured; and comparing a list of one or more disease names generated from a current medical examination image with a list of one or more disease names generated from a previous medical examination image, wherein, when an amount of change is greater than or equal to a threshold, a previous medical examination history before the current medical examination is not referred to even when the disease of the previous medical examination is not completely cured and the excluded disease name is determined regardless of the previous medical examination history.

* * * * *